US010101258B2

(12) United States Patent
Kaufman et al.

(10) Patent No.: US 10,101,258 B2
(45) Date of Patent: Oct. 16, 2018

(54) DETECTION SYSTEM FOR DETERMINING FILTERING EFFECTIVENESS OF AIRBORNE MOLECULAR CONTAMINATION

(71) Applicant: TSI, Inc., Shoreview, MN (US)

(72) Inventors: Stanley L. Kaufman, New Brighton, MN (US); David Y. H. Pui, Medina, MN (US); Chang Hyuk Kim, Minneapolis, MN (US)

(73) Assignee: TSI, Incorporated, Shoreview, MN (US)

( * ) Notice: Subject to any disclaimer, the term of this patent is extended or adjusted under 35 U.S.C. 154(b) by 219 days.

(21) Appl. No.: 14/837,650

(22) Filed: Aug. 27, 2015

(65) Prior Publication Data

US 2016/0061709 A1    Mar. 3, 2016

Related U.S. Application Data

(60) Provisional application No. 62/042,933, filed on Aug. 28, 2014.

(51) Int. Cl.
    *G01N 15/08*    (2006.01)
    *G01N 33/00*    (2006.01)
    *B01D 53/04*    (2006.01)

(52) U.S. Cl.
    CPC ....... *G01N 15/082* (2013.01); *G01N 33/0011* (2013.01); *B01D 53/04* (2013.01);
    (Continued)

(58) Field of Classification Search
    CPC .......... G01N 15/082; G01N 2015/084; G01N 2223/1016; G01N 23/02; G01N 33/0011;
    (Continued)

(56) References Cited

U.S. PATENT DOCUMENTS 4,761,074 A * 8/1988 Kohsaka ................ G01N 15/06
                                                356/336
4,917,862 A * 4/1990 Kraw ..................... B01D 46/10
                                                422/122
(Continued)

OTHER PUBLICATIONS

Kim et al., "AMC detection method using gas-to-particle conversion under soft X-ray irradiation", Particle Technology Laboratory, University of Minnesota and Institute of Energy and Environmental Technology e. V. (IUTA), 44th CFR Meeting, Oct. 18, 2013 (34 pages).

(Continued)

*Primary Examiner* — John Fitzgerald
*Assistant Examiner* — Truong D Phan
(74) *Attorney, Agent, or Firm* — Kagan Binder, PLLC

(57) ABSTRACT

A novel filter effectiveness detection method for AMCs (Airborne Molecular Contaminations) is provided herein, which is on-line, economical and applicable for diverse AMCs, using gas-to-particle conversion with soft X-ray irradiation radiation. In one embodiment, this method was conducted through AMC filter evaluations comparing two granular activated carbons (GACs), which are widely used AMC filter media, challenged with sulfur dioxide ($SO_2$), which is one of the major known AMCs in cleanrooms. Using this method, the concentration of gaseous $SO_2$ was assessed in terms of particle volume concentrations after the gas-to-particle conversion assisted by the soft X-ray irradiation. The results of this detection method showed high sensitivity to $SO_2$, down to parts per trillion-levels, which are levels that are too low to be detectable by currently available commercial gas sensors.

20 Claims, 7 Drawing Sheets

(52) U.S. Cl.
CPC .. *B01D 2253/102* (2013.01); *B01D 2257/302* (2013.01); *G01N 2015/084* (2013.01); *G01N 2223/1016* (2013.01); *Y02A 50/248* (2018.01)

(58) Field of Classification Search
CPC ......... G01N 2001/2223; G01N 1/2202; G01N 15/06; G01N 1/2273; G01N 1/24; G01N 33/2858; G01N 15/04; G01N 15/0656; G01N 15/0618; G01N 33/04; G01N 15/0893; G01N 15/02; G01N 15/0272; G01N 27/622; B01D 2253/102; B01D 2257/302; B01D 53/04; A61M 5/1689; G01F 1/704; G01F 13/00; G01P 15/132; G01P 15/093; G01P 15/18; G01P 15/08; G01P 15/0894; G01C 19/58; H01J 49/0036; H01J 49/424
USPC ......... 73/28.01, 31.01, 61.42, 61.71, 861.41, 73/514.19, 514.25, 865.5; 250/282; 95/69; 356/437, 450
See application file for complete search history.

(56) References Cited

U.S. PATENT DOCUMENTS

| | | | | |
|---|---|---|---|---|
| 5,399,267 | A * | 3/1995 | Wang | B09C 1/02 210/604 |
| 8,474,304 | B2 * | 7/2013 | Knopf | G01N 1/2247 73/28.04 |
| 2006/0044548 | A1 * | 3/2006 | Lee | G01F 1/00 356/28 |
| 2006/0144224 | A1 * | 7/2006 | Howard | B01D 53/02 95/8 |
| 2006/0150754 | A1 * | 7/2006 | Burtscher | B03C 3/08 73/865.5 |
| 2006/0266132 | A1 * | 11/2006 | Cheng | G01N 15/0266 73/865.5 |
| 2007/0054803 | A1 * | 3/2007 | Miyairi | B01D 46/2429 502/439 |
| 2007/0111150 | A1 * | 5/2007 | Hijikata | C09C 1/50 431/350 |
| 2008/0053195 | A1 * | 3/2008 | Matter | C09C 1/50 73/28.01 |
| 2010/0001184 | A1 * | 1/2010 | Chen | G01N 15/0266 250/307 |
| 2010/0071554 | A1 * | 3/2010 | Pfeffer | B01D 39/06 95/275 |
| 2010/0298134 | A1 * | 11/2010 | De Leede | B01D 53/02 502/402 |
| 2011/0189460 | A1 * | 8/2011 | Chavdar | F16D 69/026 428/292.1 |
| 2012/0241601 | A1 * | 9/2012 | Kaufman | G01N 21/45 250/282 |
| 2013/0061659 | A1 * | 3/2013 | Ajay | G01N 1/2205 73/28.04 |
| 2013/0174643 | A1 * | 7/2013 | Wang | G01N 15/0272 73/28.04 |
| 2013/0186269 | A1 * | 7/2013 | Cheng | B01D 53/228 95/47 |
| 2013/0313196 | A1 * | 11/2013 | Hufen | C02F 1/441 210/652 |
| 2014/0174154 | A1 * | 6/2014 | Marra | G01N 1/2273 73/31.01 |
| 2014/0227861 | A1 * | 8/2014 | Wu | H01J 37/3211 438/468 |
| 2015/0097048 | A1 * | 4/2015 | Linnell | B05B 7/0483 239/8 |

OTHER PUBLICATIONS

Kim et al., "AMC detection method using gas-to-particle conversion under soft X-ray irradiation", Particle Technology Laboratory, Mechanical Engineering, University of Minnesota, 45th CFR Meeting, May 16, 2014 (23 pages).

* cited by examiner

DETECTION SYSTEM FOR DETERMINING FILTERING EFFECTIVENESS OF AIRBORNE MOLECULAR CONTAMINATION

PRIORITY CLAIM AND RELATED APPLICATION

The present nonprovisional patent application claims the benefit of and priority to, under 35 USC § 119(e), U.S. Provisional Patent Application No. 62/042,933, filed Aug. 28, 2014, entitled "DETECTION METHOD AND SYSTEM FOR FILTERING EFFECTIVENESS OF AIRBORNE MOLECULAR CONTAMINATION." This application is also related to US Publication 2012/0241601 with Ser. No. 13/238,196, which is hereby incorporated by reference in its entirety.

BACKGROUND

Over the last two decades, the integration and performance of semiconductor chips have been improved dramatically by employing advanced photolithography technologies to transmit smaller patterns from masks to silicon wafers, which facilitated the advances of modern electronic devices such as computers, mobile-phones and TVs. In the semiconductor industry, avoiding particulate contaminations is critical to enhancing the yield of products because the deposited particles on masks and wafers can cause defects of semiconductors, thus increasing manufacturing costs. Therefore, many efforts have been made to develop filtration systems including high efficiency particulate air (HEPA) and ultra-low particulate air (ULPA) filters for eliminating particulate contaminations.

However, as shorter wavelength ultraviolet (UV) light sources, such as a 248 nm KrF and 193 nm ArF excimer laser, are used in the advanced photolithography, new contamination problems have been highlighted in cleanrooms, which are known as airborne molecular contaminations (AMCs). AMCs represent a wide range of gaseous contaminants at very low concentrations, down to parts per billion (ppb, $10^{-9}$) or parts per trillion (ppt, $10^{-12}$) levels in cleanrooms. Semiconductor Equipment and Materials International (SEMI) categorizes AMCs into four groups, i.e. acids, bases, condensables and dopants by the standard, SEMI F21-95. AMCs can originate from inside and outside cleanrooms and can include wet chemicals of the semiconductor manufacturing processes, air pollutants or construction materials. Personnel working in cleanrooms are also major sources of AMCs. Even though the concentrations of AMCs are extremely low, they may lead to an undesired doping of the semiconductors. Additionally, particles or surface film can form when gaseous AMCs are exposed to the UV lights of the photolithography. These unintentionally synthesized particles cause defects and failures of optical systems and/or patterned silicon wafers. Due to the adverse effects of AMCs, monitoring and controlling of AMCs are now important issues in the semiconductor industry. Furthermore, AMCs are still not well understood, which makes them difficult to monitor and control. While the detailed processes leading to particle formation is the subject of ongoing research, it is clear that they originate from gases because they cannot be eliminated by particle filtering.

Existing work in the area of particle contamination produced by AMCs uses sophisticated and expensive analytical methods such as gas chromatography (GC), TOF-SIMS, and other methods to identify gaseous chemical species present regardless of whether these species cause particle or film deposition. These methods suffer from lack of knowledge of what contaminants will form the deposits. Attempts to discover which species are correlated with the particle formation ensue. Ultimately this could lead to understanding the chemical reactions and pathways leading to particle or film deposition, but it is a long and difficult process.

Nevertheless, only a few detection methods, such as UV fluorescence—analysis and gas-chromatography-mass spectroscopy (GC-MS), have been used to monitor AMCs in cleanrooms as per the recommendation by the international technology roadmap for semiconductors (ITRS). Although a UV fluorescence analyzer is relatively inexpensive, its detection capabilities are limited as most uses revolve around detecting sulfur-containing inorganic compounds such as sulfur dioxide ($SO_2$). In addition, GC-MS is an off-line detection method which determines average contamination levels for long sampling time. Other gas detection and analysis methods, chemical ionization mass spectroscopy (CI-MS) or proton transfer reaction mass spectroscopy (PTR-MS) are frequently used in the field of atmospheric sciences, but they are seldom applied for detecting AMCs in cleanrooms due to their limitations such as fragmentation (CI-MS), proton affinity (PTR-MS) as well as costs. A detection method which is economical, on-line and applicable for diverse AMCs including inorganics and organics, is not available for use in cleanroom applications.

For controlling AMC levels in cleanrooms, chemical filters, which capture AMCs by adsorption, have been developed and installed in cleanrooms in addition to the particle filters. Because the adsorption efficiency depends on the porosity and specific surface area of the media, granular activated carbons (GACs) are widely used as chemical filter media. Depending on the chemical nature of AMCs (when it is known), GACs are modified by chemical treatments or coating catalysts to enhance their adsorptive performance. Sometimes, new filtration systems are designed to remove particular AMCs. For evaluating the improved performance of the modified chemical filters, reliable detection methods are also highly desired.

Methods and/or systems for detection and elimination of particles and films formed from AMCs that are more efficient and cost effective would be advantageous. Efficient and cost-effective methods and systems for detection of particles and films formed from AMCs would also be an advantageous capability.

SUMMARY

An advantage of the teachings herein is the development of a new detection method through gas-to-particle conversion assisted by soft X-ray irradiation, which is economical, on-line and applicable for diverse AMCs with a detection limit down to ppt-levels, better than existing methods.

The system and method described herein is applicable to evaluating the filtration performance of chemical filters in filtering out AMCs and as a reliable detection method. In one example embodiment, GACs (granular activated carbons) were challenged by $SO_2$ (sulfur dioxide) to make comparisons in implementing the method described herein.

Various embodiments of the invention include methods and systems for detecting the presence of AMCs. In one example embodiment of the invention, there is provided a novel AMC detector using soft X-ray irradiation assisted gas-to-particle conversion in an on-line form factor. The effectiveness and operability of this AMC detector was tested in evaluation tests for two different GAC material filters using $SO_2$ as the AMC. The filtration performance of the different GAC material filters was determined in terms of particle volume concentrations which were generated from the gas mixtures downstream of the GAC material holder in the conversion chamber under the soft X-ray irradiation. The results at different evaluation conditions showed a consistent relative performance between the two GAC material filters. When [$V_{p,net}$] (net particle volume) values were converted into [$SO_2$] using the empirical correlation equations, the calculated gas concentrations showed good correlation at ppb (parts per billion) levels. In addition, the correlation equation (1) was extrapolated to gas concentrations below those measurable by a commercial gas analyzer and the results showed the surprisingly high sensitivity of this detection method for $SO_2$, down to ppt (parts per trillion) levels. Although the results at ppt levels could not be quantitatively confirmed due to the lack of calibration data from any available $SO_2$ monitor, the results qualitatively agreed well with the results from measurements at higher concentrations and the dilution factors used. In a related embodiment, this invention is used as a method to detect diverse AMCs such as aromatic organics and any VOCs (volatile organic compounds) which can be converted into particles through gas-to-particle conversion, in addition to an inorganic AMC, such as $SO_2$.

In one example embodiment, a system for assessing airborne molecular contamination (AMC) filter effectiveness is provided that includes at least one granular activated carbon filter device adapted to receive an AMC gas/humid air gas mixture and a a treatment chamber with a soft X-ray ionizing source that receives an output gas flow from the activated carbon filter. The system further includes a diluter assembly that dilutes an ionized gas sample with particles received from the treatment chamber and a particle measurement system adapted to measure particle characteristics of a sample received from the treatment chamber. In a related embodiment, the particle measurement system of the assessing system is selected from the group consisting of a condensation particle counter, an ultrafine condensation particle counter (UCPC) and an electrical aerosol detector. In yet another related embodiment, the particle measurement system of the assessing system includes a scanning mobility particle sizer that receives the ionized gas sample with particles directly from the treatment chamber.

In another example embodiment, method is provided for detecting airborne molecular contamination (AMC) through gas to particle conversion using soft X-ray irradiation that includes the steps of providing a sample gas flow including AMCs and then mixing humidified air with the sample gas flow including the AMCs to form an AMC/humid air mixture. The method also includes directing the AMC/humid air mixture into a treatment chamber having a soft X-ray irradiation device as an ionizing radiation source, wherein gas to particle conversion occurs as the sample gas mixture is exposed to the ionizing radiation. The method further includes measuring particle size distributions on an output sample of gas flow with particles received from the treatment chamber using a scanning mobility particle sizer. In a related embodiment, the method includes the step of bifurcating the output sample gas flowing from the treatment chamber such that a portion of the sample gas is directed to a diluter assembly operatively coupled to a condensation particle counter assembly.

BRIEF DESCRIPTION OF THE DRAWINGS

Other important advantages of the invention will be apparent from the following detailed description of the invention taken in connection with the accompanying drawings in which.

DESCRIPTION OF PREFERRED EMBODIMENTS

Following are more detailed descriptions of various related concepts related to, and embodiments of, methods and apparatus according to the present disclosure. It should be appreciated that various aspects of the subject matter introduced above and discussed in greater detail below may be implemented in any of numerous ways, as the subject matter is not limited to any particular manner of implementation. Examples of specific implementations and applications are provided primarily for illustrative purposes.

Particle formation from gases, such as binary homogenous nucleation (BHN) of sulfuric acid and water ($H_2SO_4/H_2O$) from $SO_2$ and secondary organic aerosols (SOAs) from hydrocarbon (HC) mixtures, can be frequently observed in the atmosphere. Many researchers working in the field of atmospheric chemistry have investigated the particle formation in the laboratory using gas-to-particle conversion process, which is the main principle of a soft X-ray irradiation assisted detection method, which uses a chamber and an external energy source such as UV light, sunlight or X-ray radiation. Using this approach, some prior art researchers have presented a detection method with a UV light for explosive materials, such as 2,4,6-trinitrotoluene (TNT), in the environment. Although some of them showed particle formations from gas contaminations at sub-ppb levels in terms of particle number concentrations, these were too low in number to detect or measure due to the low photon energy of UV light. This means low sensitivity to gas compounds if these methods are used for gas detection. Therefore, soft X-ray irradiation was used to obtain higher sensitivity to gas compounds for the new AMC detection method developed herein.

Figure 1A:
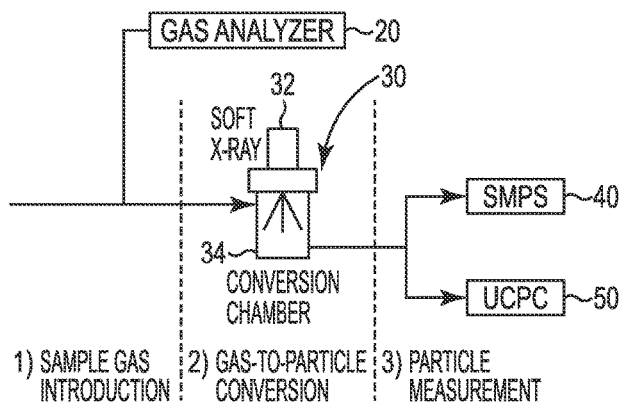
FIG. 1A-1B are schematic views of a general soft X-ray irradiation system for detecting AMCs and an improved soft X-ray irradiation AMC detection system in accordance with the invention.

Referring now to the Figures, FIG. 1A illustrates a schematic diagram of a soft X-ray irradiation assisted detection system 10 which uses a gas analyzer 20, a gas-to-particle conversion unit 30 using a photoionizer (Sunje Hi Tek, SXN-10F) 32, which emits 9.5 keV soft X-ray in a conversion chamber 34. The energy of the soft X-ray irradiation corresponds to a sub-nanometer wavelength, which is much shorter than the commercial UV lights, such as ArF (248 nm) and KrF (193 nm) in photolithography. The extremely short wavelength makes it possible to see smaller features and write smaller patterns as in microscopy and lithography, respectively. The soft X-ray photons have sufficient energy (in the KeV range) to ionize any gas molecules present, while their large absorption cross section makes them highly effective at producing ions within the limited chamber volume. Since alpha particles are also very effective ionizers at short range, an alpha emitter such as 241 Am could also serve this purpose, but with all of the drawbacks of radioactive materials. Other forms of ionizing radiation such as gamma rays, hard X-rays and beta emissions are generally less effective due to their smaller absorption cross sections. Further, particle formation under soft X-ray irradiation matches one of the worst-case AMC-related problems in cleanrooms because soft X-ray irradiation is rapidly becoming one of the candidate light sources for the next generation of photolithography. The cylindrical conversion chamber 34, where particles are generated under the soft X-ray irradiation, has a dimension of $\Phi$ 127×203 mm ($\Phi$ 5×8 in.). To minimize outgassing from the system, the chamber and tubing were made of stainless steel and baked at 200° C. for at least 2 hours before experiments to eliminate contaminants desorbed from the conversion chamber wall.

In an example experiment, target gas mixtures for the detection method were sampled by vacuum pumps in the particle measurement systems including an ultrafine condensation particle counter 50 (UCPC, TSI model 3776) and a scanning mobility particle sizer 40 (SMPS, TSI model 3936N76) and introduced into the conversion chamber 34. In other related embodiments, other CPCs are used as well as an EAD (electronic aerosol detector) as substitutes for the UCPC and the SMPS. The particle generation in the chamber was monitored by the UCPC, and then the size distributions of particles were measured by the SMPS. The aerosol flow rate of the UCPC was fixed at 1.5 lpm (liters per minute) and the aerosol flow rate and the sheath flow rate of the SMPS were set at 1.5 lpm and 15 lpm, respectively, with constant measuring times (120 s (seconds) for the scan time and 15 s for the retrace time). With these settings, the SMPS measured number size distributions of generated particles in a size range from about 2.5 nm (the cutoff size of the SMPS used) to about 65 nm (nanometer). All of the particle number and volume concentrations described herein were obtained from the size distributions measured by the SMPS. Depending on the nature and concentration of the target gas, appropriate gas analyzers can be used to measure corresponding gas concentrations simultaneously.

Figure 1B:
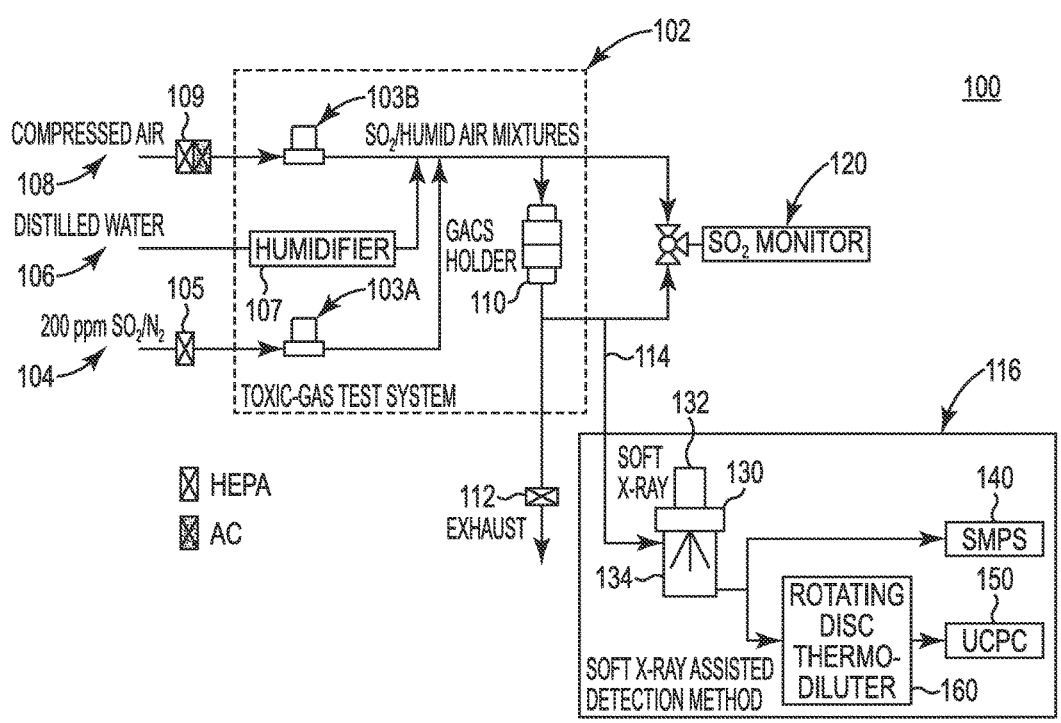

The testing of an improved soft X-ray irradiation assisted detection system 100 was conducted through the evaluation tests of GAC material filters using an experimental setup as shown in FIG. 1B. In this example embodiment, GAC material filters and the $SO_2$ gas were selected for testing because they are widely used and well-known materials. However, the materials are not limited to those tested in this example. $SO_2$/compressed air mixtures at different conditions in Table 2 were prepared by the toxic-gas test system 102 (dashed-line box).

TABLE 2

Conditions of the GAC evaluation tests at 50 ± 5% RH and 23 ± 2° C.

| No. | Face velocity (m/s) | Inlet $SO_2$ concentration (ppm) | Height of GACs (mm) |
|---|---|---|---|
| 1 | 0.33 | 10 | 5 |
| 2 | 0.2 | 10 | 20 |
| 3 | 0.9 | 1 | 20 |

The compressed air 108, which was used as a carrier gas, was purified by a combination of commercial HEPA and activated carbon (AC) filters 109 before entering system 102 and then was conditioned at 50±5% RH and 23±2° C. using the embedded humidifier 107 (and distilled water 106) of the system. The hygroscopic conditions were controlled based on a generally accepted test standard for gas filters. Next, the purified 108 and humidified air 106 was mixed with a 200 ppm $SO_2/N_2$ (blended by Air Liquide) 104 from a compressed gas cylinder (using flow controllers 103A and 103B) and introduced to a GAC packed bed holder 110. Two different GAC material bed filters were pre-conditioned over 48 hours in a climate chamber at 50±5% RH and 23±2° C. before all tests were performed to avoid RH (relative humidity) effects on the filtration performance. Each GAC bed filter was then mounted into a GAC material holder with a diameter of 50 mm. The $SO_2$/compressed air mixtures were bifurcated such that part of the flow passed through an SO2 monitor 120 and the other flow passed through GAC material holder 110 (GAC material holder 110 has excess flow coming out an exhaust 112). A flow 114 downstream of GAC material holder 110 was then sampled and analyzed by the soft X-ray irradiation assisted detection system 116 (straight-line box) using a soft X-ray irradiation device 132 as the gas flow passes through chamber 134 the outflow of which is split and directed to an SMPS device 140 and a combination diluter assembly 160 and CPC device 150. In this example embodiment, diluter assembly 160 includes a rotating disc diluter for reducing the particle number concentration of sample gas being introduced into CPC 150. If the number concentrations of generated particles were higher than the detection limit ($3\times10^5$ #/cm$^3$) of the UCPC, the rotating disc thermodiluter (TSI model 379021) 160 was used to dilute the particle concentrations before going into UCPC 150. Simultaneously, $SO_2$ concentrations ([$SO_2$]) of all gas mixtures were measured by an ambient $SO_2$ monitor 120 (HORIBA, APSA-370), which had a lower detection limit of 1 ppb. The measured [$SO_2$] reduced through adsorption by the GAC material holders (or filters) were compared to the particle volume concentrations ([$V_p$]). In a related embodiment, diluter assembly 160 includes a dilution bridge arrangement.

The residence time in conversion chamber 134 can be changed by the gas volume flow rate in the chamber and is one of the important factors for the particle formation. However, the pressure in the GAC holder of the toxic-gas test system was controlled at slightly lower than the ambient pressure for the safety issue that may be caused by leaked toxic gases. Therefore, the gas volume flow rate was determined only by the vacuum pumping speed (1.5 lpm) of the UCPC and the SMPS to sample gas mixtures. Therefore the bulk residence time of this example was about 100 s.

Due to the high photon energy of the soft X-ray irradiation, particles can be formed from intrinsic, uncontrolled contaminants of the carrier gases in addition to the intentionally-input AMCs. In related embodiments, the baseline particles on the particle generation from AMCs of three gas mixtures were tested and prepared at 50 ppb [$SO_2$] with different carrier gases such as $N_2$ (Air Liquide, N50), synthetic air (Air Liquide, Alphagaz) and compressed air (by a basic home compressor) as shown in Table 1.

TABLE 1

Baseline particle concentrations (0 ppb SO₂) and net particles concentrations generated from SO₂ (50 ppb SO₂) with different carrier gases at 1.5 lpm, 50 ± 5% RH and 23 ± 2° C.

| Carrier gas species | $SO_2$ concentration (ppb) | Particle number concentration (#/cm³) | Particle volume concentration (nm³/cm³) |
|---|---|---|---|
| $N_2$ | 0 | $2.75 \times 10^5 \pm 5.3 \times 10^4$ | $6.3 \times 10^7 \pm 3.5 \times 10^7$ |
| | 50 | $3.92 \times 10^6 \pm 3.84 \times 10^5$ | $3.76 \times 10^9 \pm 3.49 \times 10^8$ |
| Synthetic air | 0 | $9.43 \times 10^5 \pm 4.77 \times 10^5$ | $3.06 \times 10^8 \pm 2.22 \times 10^8$ |
| | 50 | $2.89 \times 10^6 \pm 4.68 \times 10^5$ | $4.26 \times 10^9 \pm 3.18 \times 10^8$ |
| Compressed air | 0 | $1.65 \times 10^6 \pm 2.5 \times 10^4$ | $4.86 \times 10^8 \pm 1.01 \times 10^8$ |
| | 50 | $3.47 \times 10^6 \pm 1.84 \times 10^5$ | $3.71 \times 10^9 \pm 4.07 \times 10^8$ |

Figure 2A:
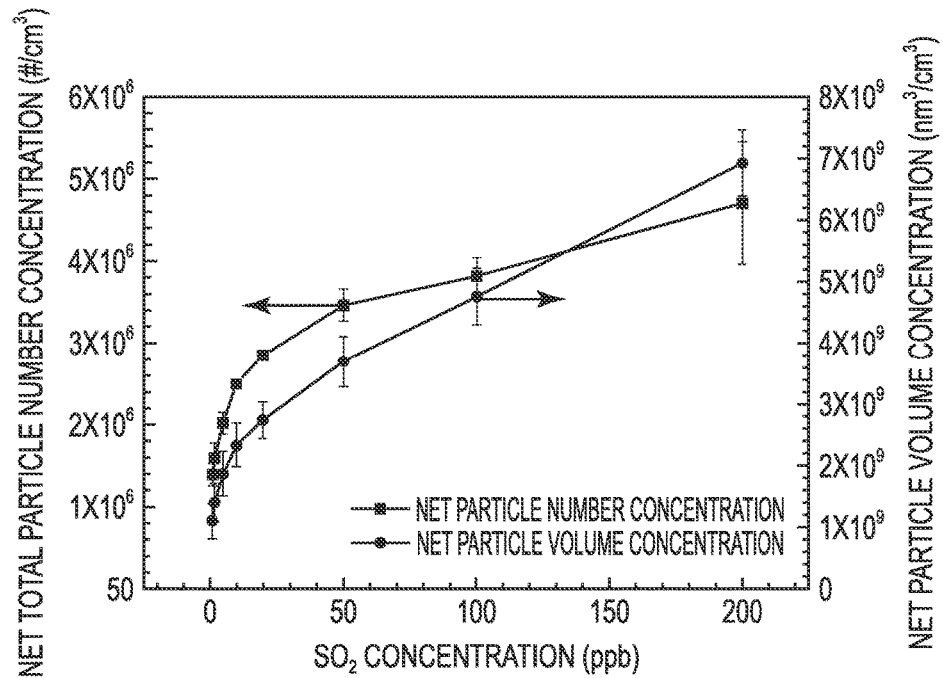
FIGS. 2A-2D are various graphs illustrating particle number and volume concentrations; size distributions; volume distributions of $SO_2$ from 1-200 ppb; and concentrations measured by $SO_2$ using correlation equations 1 and 2 herein, respectively.

The relative humidity (RH) and temperature of all gas mixtures were about 50±5% RH and 23±2° C., respectively. The RH for the gas mixtures with $N_2$ and synthetic air was conditioned using a humidifier of basic construction and the compressed air was conditioned using the embedded humidifier in the toxic-gas test system described above. Correlation equations between $SO_2$ and particle volume concentrations were developed through the various examples to improve the performance and outcomes of the AMC detection system. In addition to the comparison of the measured $[SO_2]$ with $[V_p]$, the $[SO_2]$ can be compared to those calculated from $[V_p]$ using empirical correlation equations between $[SO_2]$ and $[V_p]$. The correlation equations were obtained by calibrating $[V_p]$ with the measured $[SO_2]$ level, which were 1, 2, 5, 10, 20, 50, 100 and 200 ppb, without the GAC holders. Measurements of particle concentrations were repeated in triplicate and results were averaged and presented as illustrated in FIG. 2A. When the calculated $[SO_2]$ levels were in the detection range of the $SO_2$ monitor, the calculated $[SO_2]$ levels were checked with $[SO_2]$ measured levels by $SO_2$ monitor 120. These correlation equations were also used to estimate $[SO_2]$ levels that were lower than the detection limit of the $SO_2$ monitor by the extrapolation.

The effect of baseline particles on the particle formation from SO was also studied with the test results for the effect of baseline particles being shown in Table 1. When only carrier gases (at 0 ppb $[SO_2]$ for each carrier gas in Table 1) were introduced to conversion chamber 134, particles were generated under the soft X-ray irradiation. The baseline particle concentrations varied with respect to the species of the carrier gas used, which increased from $N_2$ to compressed air. This implies that the total concentration of intrinsic contaminations in carrier gases, in this example, were different because the hygroscopic conditions of carrier gases were fixed at 50±5% RH and 23±2° C. Total particle concentrations were at 50 ppb of $[SO_2]$ also showed the same order as baseline particle concentrations. However, when net particle concentrations (at 50 ppb $[SO_2]$ for each carrier gas in Table 2), which were determined by subtracting baseline particle concentrations (at 0 ppb $[SO_2]$) from the total particle concentrations (at 50 ppb $[SO_2]$), were calculated, all gas mixtures showed more or less concentrations. Based on the results in Table 1, although baseline particles can be generated from the intrinsic contaminants of the carrier gases and the concentrations of them were different, the effect of baseline particles on the particle formation from the target AMC was not significant, at least for particles produced from $SO_2$. Therefore, the net particle concentrations were used to eliminate the unwanted effects of the intrinsic contaminants of the compressed air on the concentration of generated particles from $SO_2$ during the evaluation tests for the GAC holders, instead of total particle concentrations.

Figure 2B:
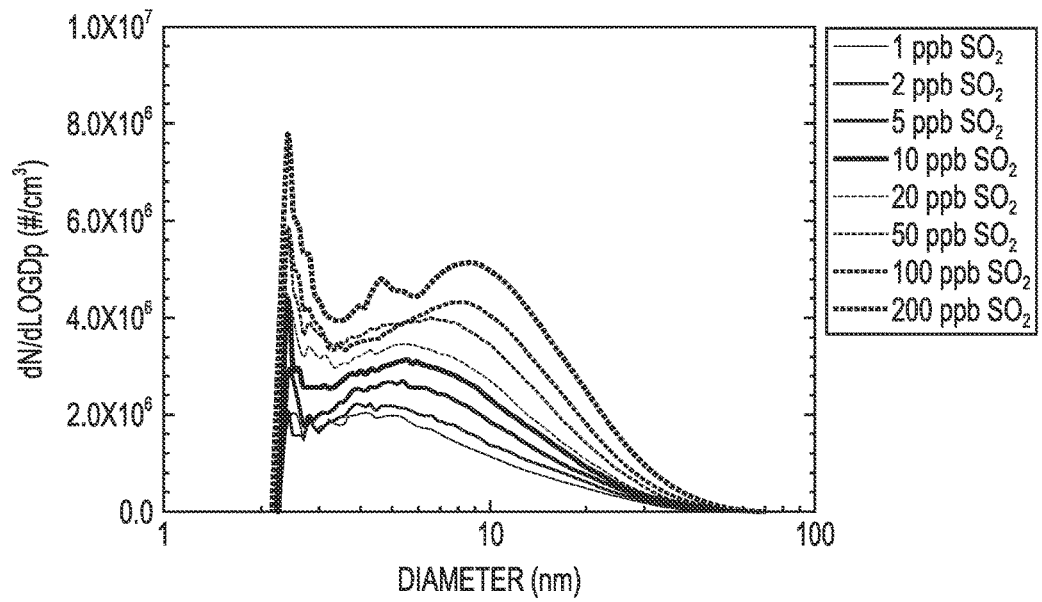
Figure 2C:
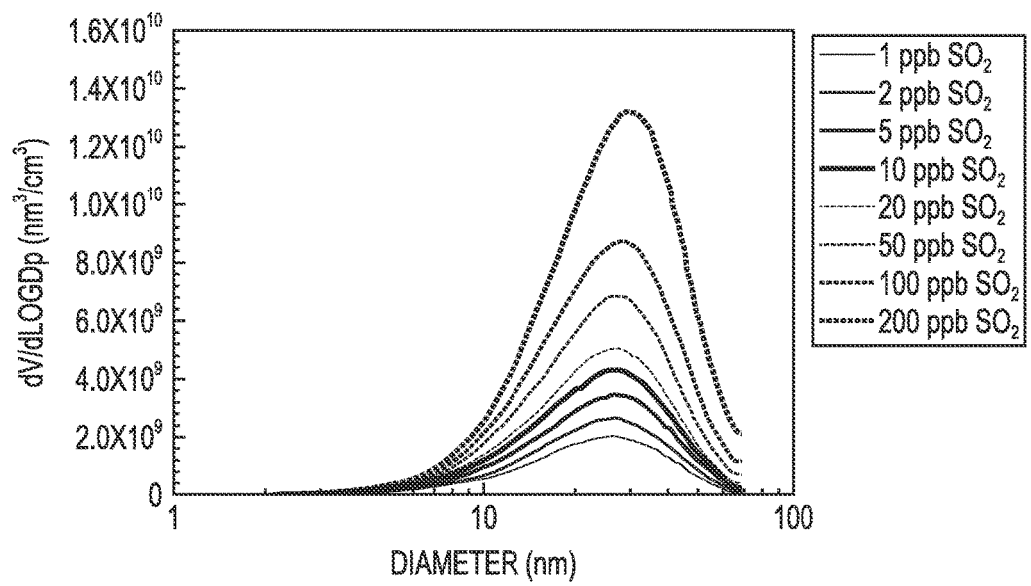

Correlation equations between $SO_2$ and particle volume concentrations were also studied and the net particle number and volume concentrations ($[N_{p,net}]$ and $[V_{p,net}]$, respectively) according to $[SO_2]$ are shown in FIG. 2A. The correlations of both net particle concentrations according to $[SO_2]$ changed from non-linear to linear relationships over 50 ppb. The non-linearity in the $[SO_2]$ range lower than 50 ppb may come from the particle transport loss on tubing walls and complicated reactions for particle generations, thereby providing the non-linearity at low levels of $[SO_2]$. The net number and volume size distributions at different $[SO_2]$ levels are depicted in FIGS. 2B and 2C, respectively. All net number size distributions in FIG. 2B had two peaks. The lower mode could only be measured down to the lower detection limit of SMPS 140, i.e. 2.5 nm, but obviously had a lower modal diameter, which is the peak of the size distribution. The second broad peak showed modal diameters ranging from 5 to 10 nm for 1 to 200 ppb, respectively. The hidden particles below the SMPS detection limit may also contribute to the non-linearity of the net particle number concentrations according to the $SO_2$ concentrations. In addition, the increasing modal diameter of the second broad peak in FIG. 2B shows that nucleation and condensation processes occurred simultaneously in conversion chamber 134. However, $[N_{p,net}]$, which was obtained by integrating each net number size distribution, on the left axis in FIG. 2A considered only the nucleation process.

On the other hand, all net volume size distributions in FIG. 2C showed single peaks at 25 nm because smaller size particles have only a negligible contribution to particle volume concentrations. In addition, $[V_{p,net}]$, which was obtained by integrating each net volume size distribution, on the right axis in FIG. 2A are related to mass balances between gas molecules and particles through the gas-to-particle conversion process because $[V_{p,net}]$ includes both nucleation and condensation processes. Therefore, correlation equations should be obtained using $[V_{p,net}]$ for more accurate results. If the exact density of measured particles is given, particle mass concentrations can be used instead of particle volume concentrations.

Figure 2D:
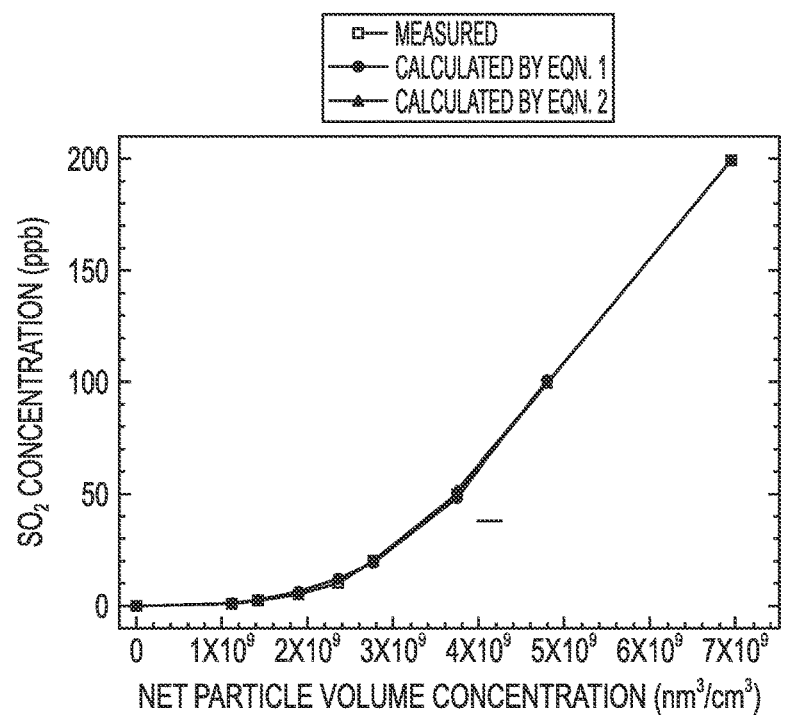

Due to the change of linearity between $[SO_2]$ (in ppb) and $[V_p]$ (in nm³/cc), the difference between the measured and calculated $[SO_2]$ levels increased as $[SO_2]$ levels increased when trying to fit the measured results in a single equation. Therefore, two empirical correlation equations were obtained by a curve-fitting mean of $[V_{p,net}]$ in the non-linear and linear regions as shown in FIG. 2D, with $R^2$ higher than 0.99.

Correlation equation 1 is as follows:

$$[SO_2] = 4.452 \times 10^{-10} [V_{p,net}] - 7.162 \times 10^{-19} [V_{p,net}]^2 + 1.006 \times 10^{-27} [V_{p,net}]^3$$

Correlation equation 2 is as follows:

$$[SO_2] = -123.37 + 4.68 \times 10^{-8} [V_{p,net}]$$

$[SO_2]$ levels according to $[V_{p,net}]$ less than $5 \times 10^9$ nm³/cm³ (corresponding to 100 ppb $[SO_2]$) were calculated using equation (1). For $[V_{p,net}]$ over $5 \times 10^9$ nm³/cm³, equation (2) was used to calculate $[SO_2]$ levels. Because there was no calibration data for $[SO_2]$ at ppt-levels, equation (1) was extrapolated to estimate unknown $[SO_2]$ at ppt-levels from $[V_{p,net}]$.

Figure 3A:
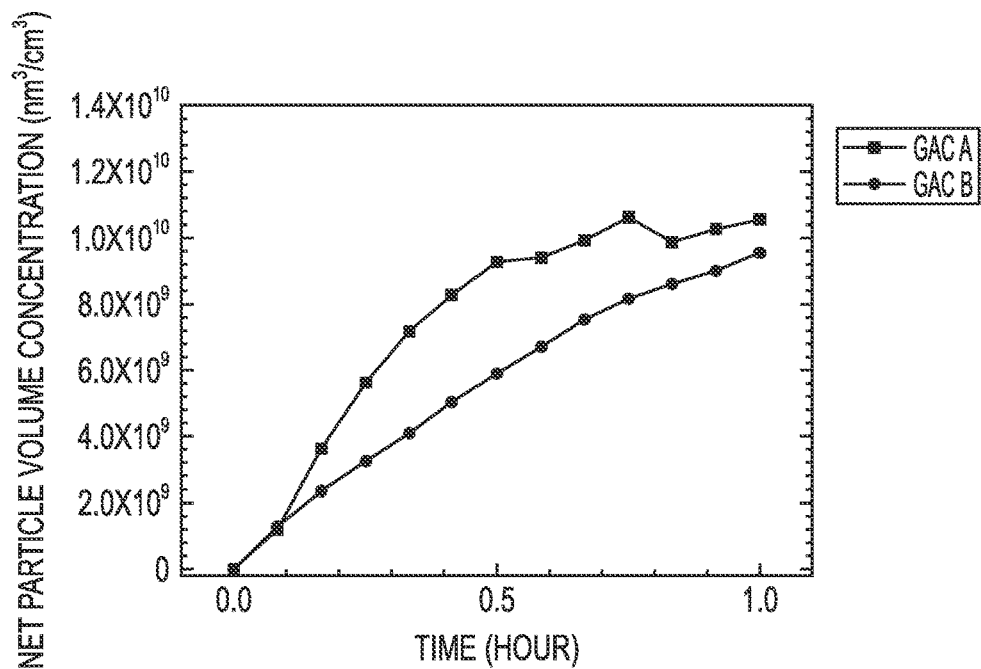
FIGS. 3A-3D are graphs illustrating test results of first condition in Table 2 for 1 hour of net particle volume concentrations; calculated $SO_2$ concentrations for GAC A material and GAC B material; and comparison calculated $SO_2$ concentrations for the GAC A material and GAC B material, respectively.
Figure 3B:
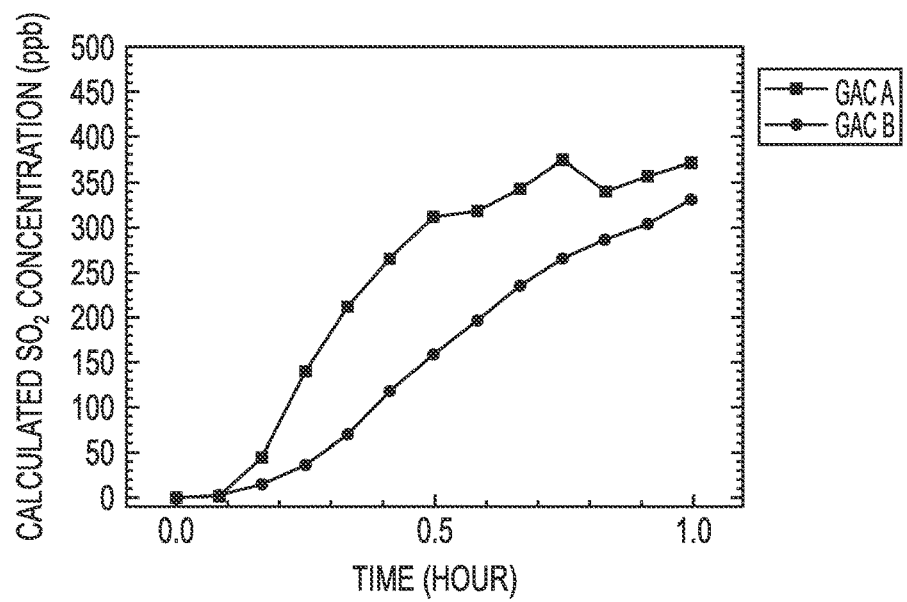
Figure 3C:
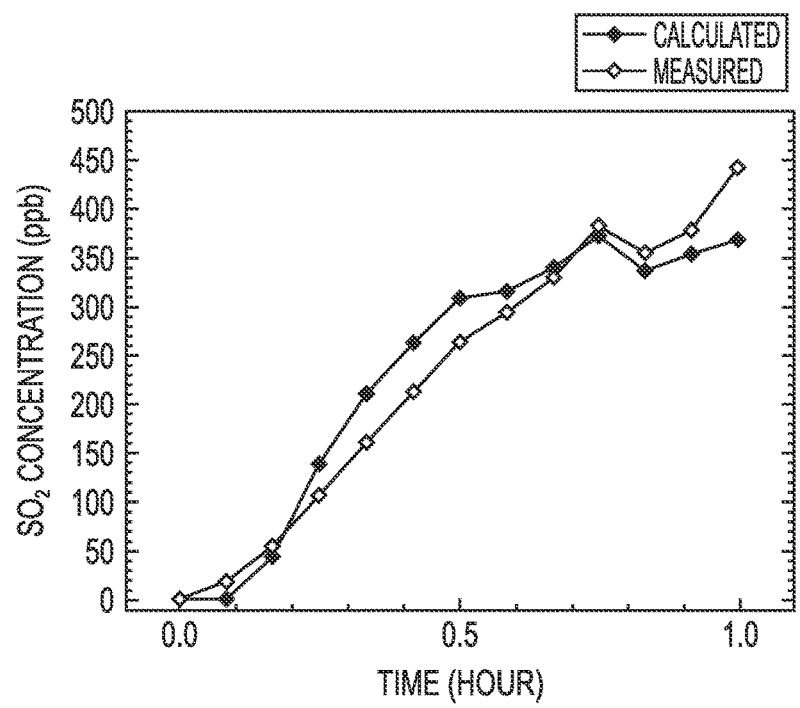
Figure 3D:
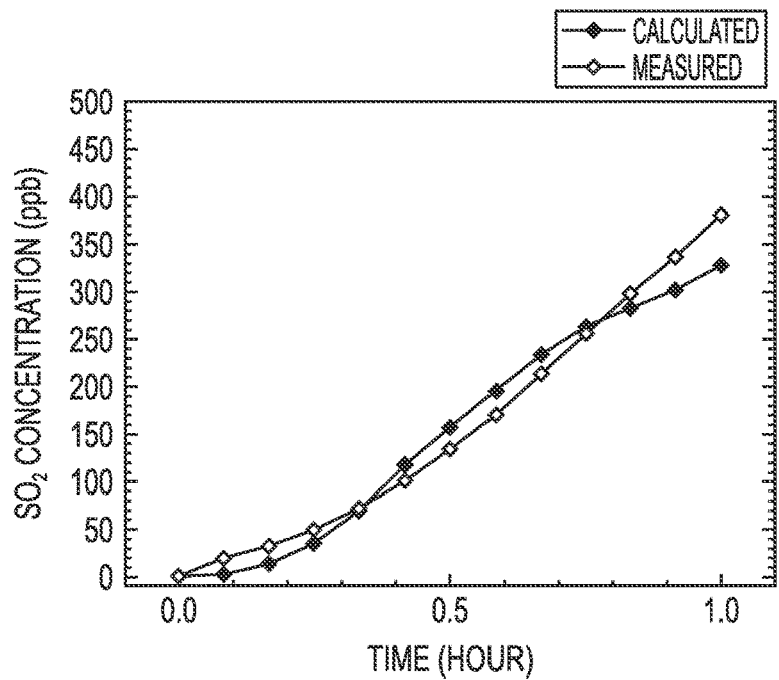

Evaluation of the performance of different GAC material holders as to $SO_2$ levels using the soft X-ray irradiation assisted AMC detection method and the correlation equations provided the results shown in FIGS. 3A-3D for the first condition in Table 2. At the condition to accelerate breakthrough of the GAC material holders with 5 mm height and 10 ppm inlet [$SO_2$], [$V_{p,net}$] for both GAC material filters increased quickly within only 1 hour as shown in FIG. 3A and [$SO_2$] levels calculated using both equation (1) and (2) from [$V_{p,net}$] in FIG. 3A were over 300 ppb after 1 hour as shown in FIG. 3B. Because both calculated [$SO_2$] levels in FIG. 3B were in the detection range of the $SO_2$ monitor, they were compared to [$SO_2$] levels measured in parallel by the $SO_2$ monitor as shown in FIGS. 3C and 3D for the GAC A and B, respectively.

In FIGS. 3C and 3D, the calculated [$SO_2$] levels and measured [$SO_2$] levels were well-matched with each other at ppb-levels. From these results, soft X-ray irradiation assisted detection system 100 combined with the correlation equations was validated to evaluate the GAC material holders, at least at ppb-levels. As shown in FIG. 3A, the GAC A material holder showed higher [$V_{p,net}$] than the GAC B material holder during the whole measurement. This shows that the GAC B material holder had better filtration performance than the GAC A material holder.

Figure 4A:
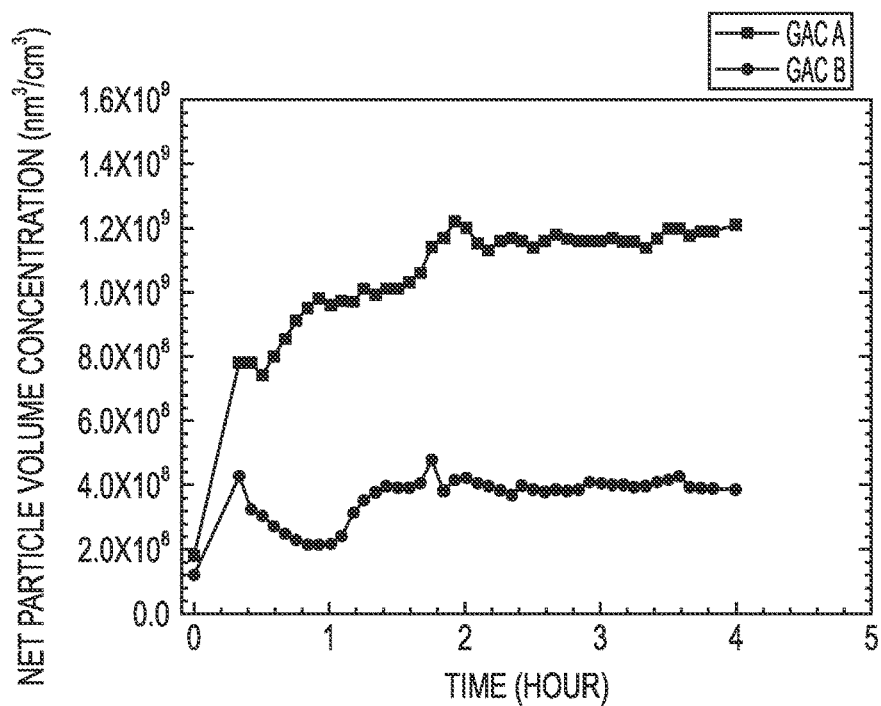
FIGS. 4A-4D are graphs illustrating test results for GAC A and GAC B materials for 4 hours net particle volume concentrations; calculated SO2 concentrations at second condition in Table 2; net particle volume concentrations and calculated SO2 concentrations at the last condition in Table 2, respectively.
Figure 4B:
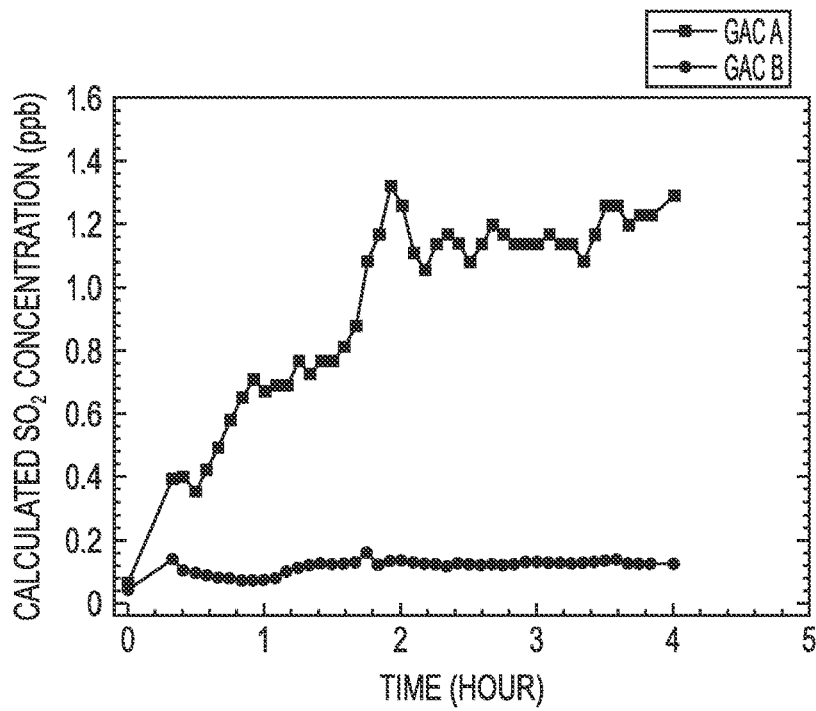
Figure 4C:
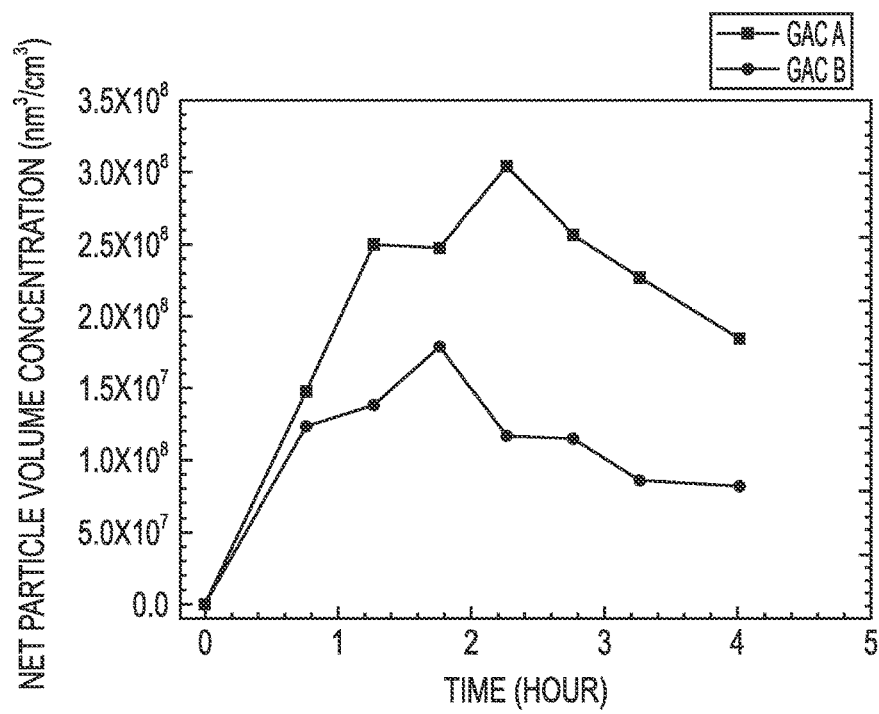
Figure 4D:
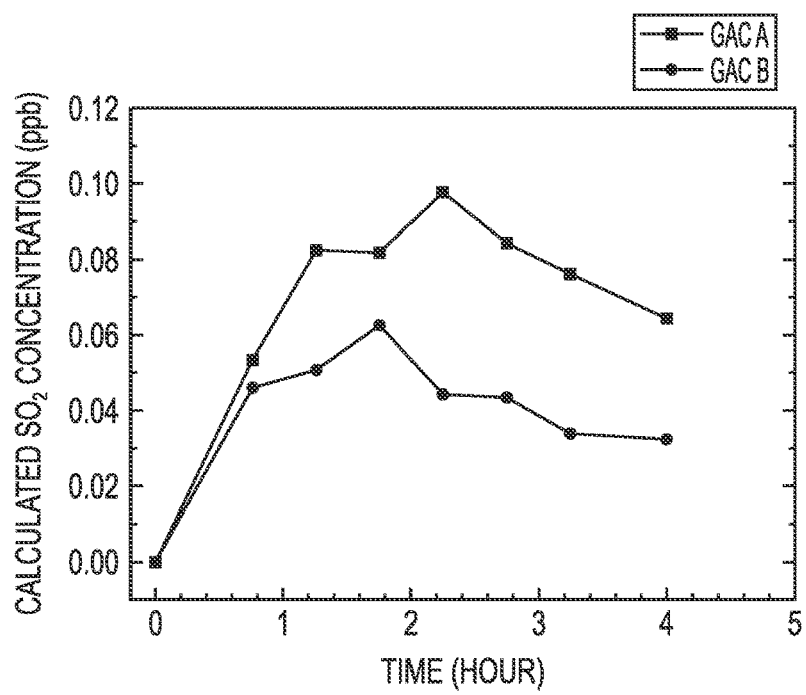

At the second evaluation condition in Table 2 to investigate the sensitivity of system 100 by increasing the height of the GAC material holders to 20 mm, [$V_{p,net}$] for the GAC A material holder decreased drastically and was saturated after 2 hours as shown in FIG. 4A. Because the final [$SO_2$] levels for the GAC A material holder, which were converted from the final [$V_{p,net}$] in FIG. 4A using equation (1), approached about 1 PO (detection limit of the $SO_2$ monitor, as shown in FIG. 4B), the $SO_2$ monitor was not applicable to measure directly [$SO_2$] levels at this condition. Therefore, all [$SO_2$] levels were calculated by extrapolating equation (1). For the GAC B material holder, [$V_{p,net}$] was three times lower than that for the GAC A material holder after 2 hours as shown in FIG. 4A. Furthermore, the highest [$SO_2$] level calculated by extrapolating equation (1) in FIG. 4B was around 120 ppt. Although all calculated [$SO_2$] levels were not quantitatively exact due to the extrapolation of equation (1), the filtration performance of the two GAC holders can be distinguished qualitatively by this detection method, which is highly sensitive to $SO_2$, down to ppt-levels. Also, at this condition, the GAC B material holder showed lower [$V_{p,net}$] than the GAC A material holder, which means better filtration performance of the GAC B material holder To check the detection sensitivity of system 100 further, the inlet [$SO_2$] decreased to 1 ppm (see the last condition in Table 2). As shown in FIG. 4C, the GAC A holder showed [$V_{p,net}$] higher than the GAC B holder during the whole measurement. Because all [$SO_2$] downstream of the GAC holders were lower than 1 ppb, [$SO_2$] of both GAC holders in FIG. 4D were also only calculated by extrapolating equation (1) from [$V_{p,net}$] in FIG. 4C and the maximum concentrations were 100 ppt and 60 ppt for the GAC A and B holders, respectively. The decrease of [$SO_2$] levels after around 2 hours might be caused by the shift of the adsorption layer of both GAC holders for the $SO_2$ gas molecules. The filtration performance of the two GAC holders can be distinguished qualitatively by this detection method again with high sensitivity to $SO_2$, down to ppt-levels. For all evaluation conditions, the relative filtration performance between the two GAC material holders was consistent, i.e. the GAC B material holder was better than the GAC A material holder as shown in FIGS. 3 and 4. Hence, the novel detection system 100 using soft X-ray irradiation is valuable to evaluate AMC filters as well as to detect $SO_2$ levels at extremely low concentrations, such as ppt-levels.

Although this detection method is highly sensitive to gaseous components, it responds selectively to gases which can undergo gas-to-particle conversion, the very definition of the troublesome AMCs. In a related embodiment additional analyzers are included to distinguish different gas compounds from their mixtures. However, this soft X-ray irradiation assisted detection method can work as a faster and easier method to control the cleanroom air quality by evaluating the installed filter media and detecting highly contaminated areas as a monitor. In particular, this method can be applied where highly sensitive and/or fast detection methods are required, e.g., in evaluating performance of adsorbent materials at ultra-low gas concentrations.

The foregoing specific embodiments of the present invention as set forth in the specification herein are for illustrative purposes only. Various deviations and modifications may be made within the spirit and scope of the invention without departing from the main theme thereof.

What we claim is:

1. A system for assessing airborne molecular contamination (AMC) filter effectiveness of an AMC filter device, the system comprising:
   at least one granular activated carbon filter device adapted to receive an AMC gas/humid air gas mixture, the activated carbon filter having an output sample gas flow after receiving the AMC air gas mixture;
   an AMC gas monitor that receives a portion of the AMC gas/humid air gas mixture;
   a treatment chamber with a soft X-ray ionizing source that receives a portion of the output sample gas flow from the activated carbon filter;
   a diluter assembly that dilutes particles formed in an ionized gas sample received from the treatment chamber; and
   a particle measurement system adapted to measure particle characteristics of particles in the ionized gas sample received from at least one of the treatment chamber or the diluter assembly, wherein an output of the AMC gas monitor is compared with an output of the particle measurement system to determine qualitatively the filter effectiveness of the activated carbon filter device.

2. The detecting system of claim 1 wherein the particle measurement system includes a scanning mobility particle sizer that receives the ionized gas sample with particles directly from the treatment chamber.

3. The detecting system of claim 1, wherein the activated carbon filter is varied in a height and a carbon particle size to change the breakthrough time of the activated carbon filter to certain AMCs.

4. The detecting system of claim 1, wherein a humidity of the AMC/humid air mixture is varied to improve AMC detection capability of the system as a function of the concentration of AMCs in the AMC/humid air mixture.

5. The detecting system of claim 1 wherein the particle measurement system is selected from the group consisting of a condensation particle counter, an ultrafine condensation particle counter (UCPC) and an electrical aerosol detector.

6. The detecting system of claim 5 wherein the diluter assembly includes a rotating disc diluter.

7. The detecting system of claim 5 further comprising a the diluter assembly coupled to the UCPC.

8. A method for detecting airborne molecular contamination (AMC) in a gas having AMCs at levels as low as in parts per trillion (PPT) through gas to particle conversion using soft X-ray irradiation, the method comprising:

providing a sample gas flow including AMCs;

mixing humidified air with the sample gas flow including the AMCs to form an AMC/humid air mixture;

directing a first portion of the AMC/humid air mixture into an AMC gas monitor and directing a second portion of the AMC/humid air mixture to a treatment chamber having a soft X-ray irradiation device as an ionizing radiation source, wherein gas to particle conversion occurs as the sample gas mixture is exposed to the ionizing radiation and particles are formed;

measuring particle size distributions of the particles in an output sample of gas flow received from the treatment chamber using a scanning mobility particle sizer;

comparing an output from the AMC gas monitor and an output from the scanning mobility particle sizer; and generating at least one correlation equation at a level of parts per billion (PPB) of AMCs measured by the AMC monitor which are correlated to particle volume concentrations, and extrapolating the correlation equation for PPT detection of AMCs in the AMC/humid air mixture.

9. The method of claim 8 further comprising the step of using particle mass concentrations to generate the at least one correlation equation where a density of the measured particles in the AMC/humid air mixture is known.

10. The method of claim 8 further comprising the step of using known levels of AMCs in the AMC/humid air mixture detectable by the AMC monitor to generate the at least one correlation equation.

11. The method of claim 8 further comprising the step of operatively coupling an activated carbon filter prior to the treatment chamber after generating the correlation equation and evaluating qualitatively a filter effectiveness of the activated carbon filter of filtering out AMCs by comparing outputs of the AMC monitor and the scanning mobility particle sizer.

12. The method of claim 8, further comprising the step of bifurcating the output sample gas flowing from the treatment chamber such that a portion of the sample gas with formed particles is directed to a diluter assembly operatively coupled to a condensation particle counter assembly.

13. The method of claim 12, wherein the diluter assembly is selected from the group consisting of a rotating disc diluter and a rotating disc thermo-diluter.

14. The method of claim 12 wherein the condensation particle counter assembly is an ultrafine condensation particle counter assembly.

15. A system for assessing airborne molecular contamination (AMC) filter effectiveness of an AMC filter device, the system comprising:

at least one granular activated carbon filter device adapted to receive an AMC gas/humid air gas mixture, the activated carbon filter having an output sample gas flow after receiving the AMC air gas mixture;

an AMC gas monitor that receives a portion of the AMC gas/humid air gas mixture;

a treatment chamber with a soft X-ray ionizing source that receives a portion of the output sample gas flow from the activated carbon filter;

a diluter assembly that dilutes particles formed in an ionized gas sample received from the treatment chamber and directs the particles in the ionized gas sample to a condensation particle counter assembly; and a particle measurement system adapted to measure particle characteristics of the particles in the ionized gas sample received from the treatment chamber, wherein an output of the AMC gas monitor is compared with an output of the condensation particle counter assembly and with an output of the particle measurement system to determine qualitatively the AMC filter effectiveness of the activated carbon filter device.

16. The system of claim 15, wherein the diluter assembly is selected from the group consisting of a rotating disc diluter and a rotating disc thermo-diluter.

17. The system of claim 15, wherein the activated carbon filter is varied in a height and a carbon particle size to change the breakthrough time of the activated carbon filter to certain AMCs.

18. The system of claim 15, wherein a humidity of the AMC/humid air mixture is varied to improve AMC detection capability of the system as a function of the concentration of AMCs in the AMC/humid air mixture.

19. The system of claim 15 wherein at least one correlation equation is generated for detecting AMCs at a level of parts per billion (PPB) of AMCs measured by the AMC monitor which are correlated to particle volume concentrations, and the correlation equation is extrapolated for a parts per trillion (PPT) detection of AMCs in the AMC/humid air mixture.

20. The system of claim 19 wherein the at least one correlation equation is generated using net particle volume concentrations of AMCs in the AMC/humid air mixture.

* * * * *